(12) United States Patent
Coussios et al.

(10) Patent No.: US 9,220,476 B2
(45) Date of Patent: *Dec. 29, 2015

(54) ULTRASOUND SYSTEMS

(75) Inventors: Constantin Coussios, Oxford (GB); Manish Arora, Oxford (GB); Natalie Hockham, Oxford (GB); Ronald Aurele Roy, Brighton, MA (US)

(73) Assignee: Isis Innovation Limited, Summerton, Oxford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/497,470

(22) PCT Filed: Sep. 20, 2010

(86) PCT No.: PCT/GB2010/051570
§ 371 (c)(1),
(2), (4) Date: Jun. 26, 2012

(87) PCT Pub. No.: WO2011/036475
PCT Pub. Date: Mar. 31, 2011

(65) Prior Publication Data
US 2012/0259222 A1    Oct. 11, 2012

(30) Foreign Application Priority Data

Sep. 22, 2009  (GB) .................... 0916634.9

(51) Int. Cl.
*A61B 8/00*    (2006.01)
*A61N 7/00*    (2006.01)
*B06B 1/02*    (2006.01)
(Continued)

(52) U.S. Cl.
CPC ... *A61B 8/00* (2013.01); *A61N 7/00* (2013.01); *B06B 1/0207* (2013.01); *A61B 17/22004*
(2013.01); *A61B 2018/00642* (2013.01); *A61B 2018/00666* (2013.01); *A61N 7/02* (2013.01);
(Continued)

(58) Field of Classification Search
USPC .......................................... 600/407, 439, 437
See application file for complete search history.

(56) References Cited

U.S. PATENT DOCUMENTS 5,158,071 A * 10/1992 Umemura et al. ................ 601/3
6,508,774 B1  1/2003 Acker et al.
(Continued)

FOREIGN PATENT DOCUMENTS

WO    WO 02051501 A1    7/2002
WO    WO 03070105 A1    8/2003
(Continued)

OTHER PUBLICATIONS

Tran et al., "Correlation Between Accoustic Backscatter Variability and Tissue Damage Produced by Pulsed Cavitational Ultrasound Therapy", Ultrasonics Symposium, 2004 IEEE Montreal, Canada, Aug. 23-27, 2004, vol. 2, pp. 1461-1464, Aug. 23, 2004.
(Continued)

*Primary Examiner* — Joel F Brutus
(74) *Attorney, Agent, or Firm* — Wegman, Hessler & Vanderburg

(57) ABSTRACT

An ultrasound system comprises a transducer, a controller arranged to generate control signals arranged to control the transducer to generate pressure waves directed at a target volume, and sensing means arranged to sense cavitation in the target volume. The controller is arranged to receive sensing signals from the sensing means and to vary the control signals in response to the sensing signals thereby to control the cavitation.

18 Claims, 6 Drawing Sheets

(51) Int. Cl.
    *A61B 17/22* (2006.01)
    *A61B 18/00* (2006.01)
    *A61N 7/02* (2006.01)

(52) U.S. Cl.
    CPC . *A61N 2007/0008* (2013.01); *A61N 2007/0039* (2013.01); *B06B 2201/76* (2013.01)

(56) References Cited

U.S. PATENT DOCUMENTS

| | | | |
|---|---|---|---|
| 2003/0093013 A1* | 5/2003 | Zhong et al. | 601/2 |
| 2004/0082857 A1 | 4/2004 | Schonenberger et al. | |
| 2004/0264293 A1* | 12/2004 | Laugharn et al. | 366/127 |
| 2006/0184075 A1 | 8/2006 | Restle et al. | |
| 2006/0264809 A1* | 11/2006 | Hansmann et al. | 604/22 |
| 2007/0083120 A1 | 4/2007 | Cain et al. | |
| 2007/0161902 A1 | 7/2007 | Dan | |
| 2007/0265560 A1 | 11/2007 | Soltani et al. | |

FOREIGN PATENT DOCUMENTS

| | | | |
|---|---|---|---|
| WO | WO 2009094554 A2 | 7/2009 | |
| WO | WO 2010052494 A1 | 5/2010 | |

OTHER PUBLICATIONS

International Search Report and Written Opinion mailed Feb. 10, 2011 for PCT/GB2010/051570 filed Sep. 20, 2010.

International Preliminary Report on Patentability mailed Apr. 5, 2012 for PCT/GB2010/051570 filed Sep. 20, 2010.

International Search Report and Written Opinion mailed Jan. 31, 2011 for PCT/GB/2010/051592 filed Sep. 22, 2010, which is the PCT Application of related U.S. Appl. No. 13/497,484, filed Jun. 26, 2012.

International Preliminary Examination Report on Patentability mailed Apr. 5, 2012 for PCT/GB2010/051592 filed Sep. 22, 2010, which is the PCT Application of related U.S. Appl. No. 13/497,484, filed Jun. 26, 2012.

Rabkin, et al., "Hyperecho in Ultrasound Images of HIFU Therapy: Involvement of Cavitation", Ultrasound in Medicine and Biology, New York, NY, US, vol. 31, No. 7, pp. 947-956, Jul. 1, 2005.

Salgaonkar et al., "Image-Guided Ex Vivo Liver Ablation by Unfocused Ultrasound Using Passive Cavitation Detection", Proc. of SPIE, vol. 6440, 2007.

Communication Pursuant to Article 94(3) EPC mailed Feb. 19, 2013 for EP 10 768 050.6.

* cited by examiner

Fig. 13
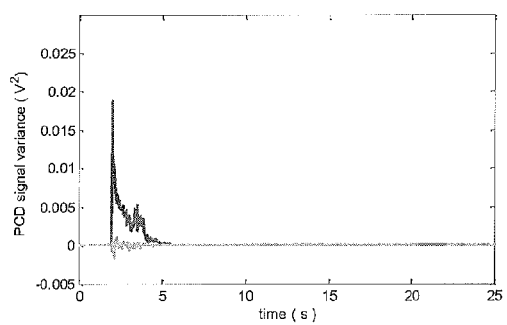
Fig. 16
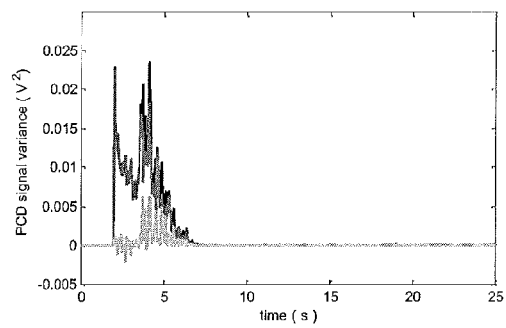
Fig. 14
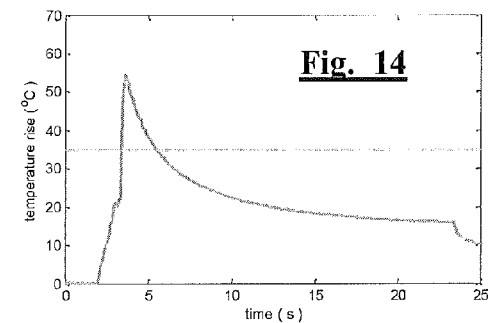
Fig. 17
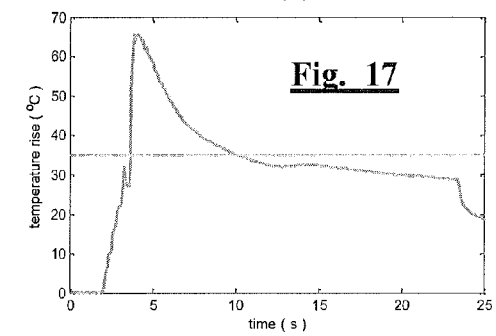
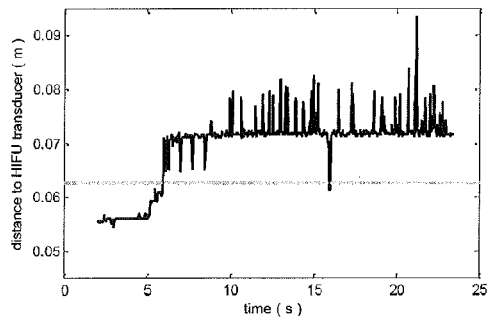
Fig. 15
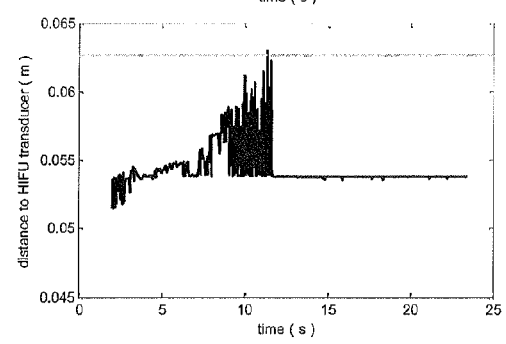
Fig. 18

ULTRASOUND SYSTEMS

CROSS-REFERENCE TO RELATED APPLICATIONS

This application claims the priority filing benefit of International PCT Application PCT/GB2010/051570 filed Sep. 20, 2010 and published under PCT 21(2) in the English language, and Great Britain Patent Application Serial No. 0916634.9 filed Sep. 22, 2009.

FIELD OF THE INVENTION

The present invention relates to ultrasound systems and in particular to therapeutic ultrasound systems arranged to generate cavitation in tissue during therapy.

BACKGROUND TO THE INVENTION

Having been traditionally perceived as a diagnostic modality, ultrasound is rapidly emerging as a most promising therapeutic tool for non-invasive ablation of cancerous and other tissues, for enhanced drug delivery, and for a range of other therapeutic applications that include thrombolysis, opening of the blood-brain barrier, tendon and bone repair, tissue erosion, vaccine delivery and acoustic haemostasis. In all of these applications, ultrasound-induced bubble activity (acoustic cavitation) has been found to play a major role in enhancing several desirable bioeffects (heating, cell permeability, drug diffusion lengthscales, etc). The term 'cavitation' is used hereafter to encompass all possible bubble behaviours in an ultrasound field, including transient or inertial cavitation; stable cavitation including shape oscillations of the bubble wall; and the response of thermally stabilized bubbles (such as boiling bubbles) in an ultrasound field. The process of cavitation itself could have been initiated through spontaneous, acoustically driven nucleation, or through the injection of stabilized gas bodies such as ultrasound contrast agents, or of solid microparticles that are designed with appropriate surface characteristics (hydrophobicity and surface roughness) to facilitate cavitation inception.

Cavitation is an inherently unstable phenomenon and, once initiated in the body (which is by itself quite unpredictable), tends to decay rapidly whilst the associated bubble cloud readily shifts positions. Being unable to sustain cavitation activity at the desired location for prolonged periods of time means that the potential benefits of cavitation cannot be fully exploited.

SUMMARY OF THE INVENTION

The present invention provides an ultrasound system comprising a transducer, a controller arranged to generate control signals arranged to control the transducer to generate pressure waves directed at a target volume, and sensing means arranged to sense cavitation in the target volume. The controller may be arranged to receive sensing signals from the sensing means and may be arranged to vary the control signals, for example in response to the sensing signals, thereby to control the cavitation.

The pressure waves may be ultrasound waves or audible sound waves.

The controller may be arranged to measure from the sensing signals the position of the cavitation, for example by measuring the position of an edge of a cavitation bubble cloud, or by imaging the cavitation bubble cloud to determine its position in two or three dimensions.

The controller may be arranged to measure from the sensing signals variations in either or both of the type and the level of cavitation activity. The controller may be arranged to control the level of cavitation activity so as to maintain at least a predetermined level of cavitation, so as to maintain the level of cavitation at or below a predetermined level, which may be zero, or so as to maintain the level of cavitation within a range between a predetermined minimum and a predetermined maximum level.

The controller may be arranged to define one or more parameters of the sensing signals, which may be a magnitude, a time-average, a mean, a peak value, a variance, or any similar metric of a sensing signal that has been post-processed in the time-domain or frequency-domain, and a target range of the one or more parameters, and to change the control signals in response to the one or more parameters being outside the respective target ranges. The target range may have an upper limit and a lower limit or it may have just an upper limit, or just a lower limit.

The sensing means may comprise at least one pressure wave detector arranged to detect pressure waves generated by the cavitation. The pressure waves may be ultrasound or audible sound waves. The controller may be arranged to measure an arrival time of pressure waves at the pressure wave detector thereby to measure the position of the cavitation.

The present invention further provides a method of controlling cavitation in a subject comprising generating pressure waves directed at a target volume, sensing changes in the cavitation in the target volume, and controlling the pressure waves in response to the changes thereby to control the cavitation. The pressure waves may be controlled by a controller, but may also, or alternatively, be controlled manually.

The present invention further provides a method of setting up a pressure wave control system comprising producing a control signal to control a pressure wave transmitter so as to produce cavitation in a subject, sensing the cavitation using sensing means arranged to output a sensing signal indicative of one or more parameters of the cavitation, varying the control signal so as to vary the cavitation, defining one or more sensing parameters of the sensing signal, measuring one or more controlled parameters of the cavitation which are to be controlled by the system, determining how the one or more sensing parameters vary with variations in the one or more measured parameters, and selecting a target value of the one or more measured parameters corresponding to a target value of the one or more sensing parameters.

For example the sensing parameter may be indicative of the level of cavitation activity. The sensing parameter may be the magnitude of the sensing signal, or a variance of the sensing signal, or the timing of the sensing signal. The sensing means may comprise a passive cavitation detector, such as a pressure sensor. The controlled parameter may comprise, for example, a temperature, or a position of the cavitation, or a cell permeability, or drug diffusion lengthscale.

Some embodiments of the present invention provide a procedure to identify the set-point or range of set-points for quantifiable cavitation activity, in order to achieve optimal energy transfer to the surrounding medium (in terms of heat, momentum transfer, tissue erosion, bubble cloud position, or whichever other quantifiable cavitation-induced effect).

Some embodiments of the invention provide an adaptive cavitation controller which varies the input signal (for example by varying one or more of the frequency, amplitude, duty cycle, pulse duration, etc.) to a single or multiple pressure wave transducers in order to maintain the level of cavitation activity as continuously detected by a single or multiple cavitation detectors within the desired range for prolonged periods of time.

The controller can be implemented for continuous or pulsed pressure wave exposure and with the intention of maintaining stable or inertial cavitation activity for a very broad range of therapeutic bioeffects, such as heating for ablation or hyperthermia, momentum transfer for drug delivery to tumours, tissue erosion by cavitation, lipolysis, thrombolysis, opening of the blood-brain barrier, acoustic haemostasis, and any other emerging application where cavitation activity is found to play a key role.

The ability to detect and quantify cavitation activity in a reproducible manner and to monitor it continuously and in real-time, in some cases whilst identifying the position of the bubble cloud using those same measurements from a passive cavitation detector, makes it possible to use this data in order to control cavitation in a closed feedback loop. In some cases, by continuously altering one or more of the amplitude, duty cycle, pulse duration and frequency of the input signal to the source pressure wave transducer, cavitation activity can be sustained over a broad range of experimental conditions.

Preferred embodiments of the present invention will now be described by way of example only with reference to the accompanying drawings.

BRIEF DESCRIPTION OF THE DRAWINGS

FIG. 13 is a graph of detector signal variance over time for different ultrasound frequencies during operation of the system of FIG. 1 without cavitation control with a first input energy;

FIG. 14 is a graph of temperature over time during operation of the system of FIG. 1 without cavitation control with the first input energy;

FIG. 15 is a graph of cavitation cloud position over time during operation of the system of FIG. 1 without cavitation control with the first input energy;

FIG. 16 is a graph of detector signal variance over time for different ultrasound frequencies during operation of the system of FIG. 1 without cavitation control with a second input energy;

FIG. 17 is a graph of temperature over time during operation of the system of FIG. 1 without cavitation control with the second input energy;

FIG. 18 is a graph of cavitation cloud position over time during operation of the system of FIG. 1 without cavitation control with the second input energy.

Referring to FIG. 1, a high intensity focused ultrasound system according to an embodiment of the invention comprises a high intensity focused ultrasound (HIFU) transducer 11 with a coaxial passive cavitation detector (PCD) 12 mounted at its centre. The ultrasound transducer 11 has a focal point 14 at which the ultrasound it produces is at the highest intensity and tissue to be treated is therefore located in a volume at and around that focal point 14. The PCD 12 comprises an ultrasound detector which is a pressure sensor arranged to output a signal having a voltage that varies with the pressure it detects. The pressure varies at the frequency of the ultrasound detected, and the sensor may include a high pass filter so as to avoid saturation by signals at the frequency of the ultrasound transducer 11, which can be around 1 MHz, being most sensitive to signals with a frequency range significantly higher than the frequency of the ultrasound transducer 11, for example around 5 to 15 MHz, which makes it sensitive to the acoustic emissions associated with inertial cavitation.

A controller 16 is arranged to drive the ultrasound transducer 11 using a drive signal. This drive signal is generated by an oscillator and has a frequency which determines the frequency of the ultrasound generated, and an amplitude which determines the intensity of the ultrasound generated. It is also pulse width modulated, and the controller is arranged to vary the pulse width and duty ratio (and hence frequency) of the drive pulses that generate pulses of ultrasound from the transducer 11.

Figure 1:
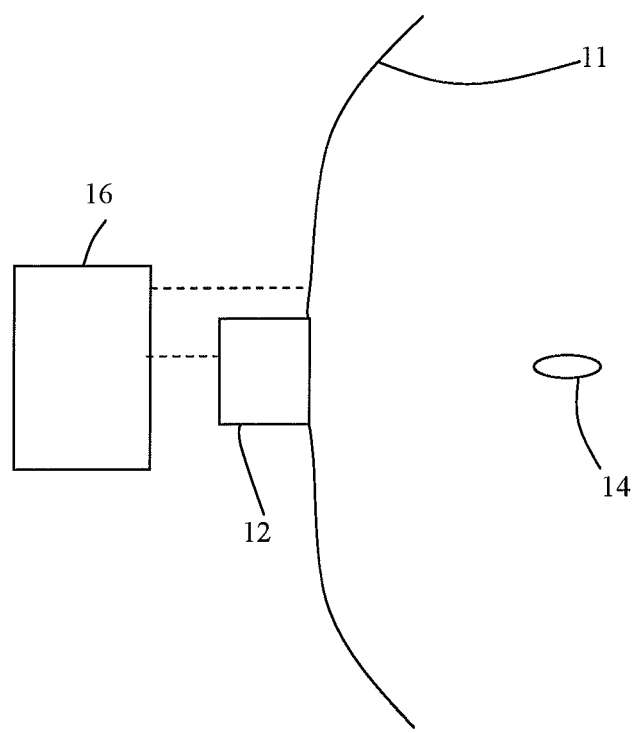
FIG. 1 is a diagram of a therapeutic ultrasound system according to an embodiment of the invention.
Figure 2:
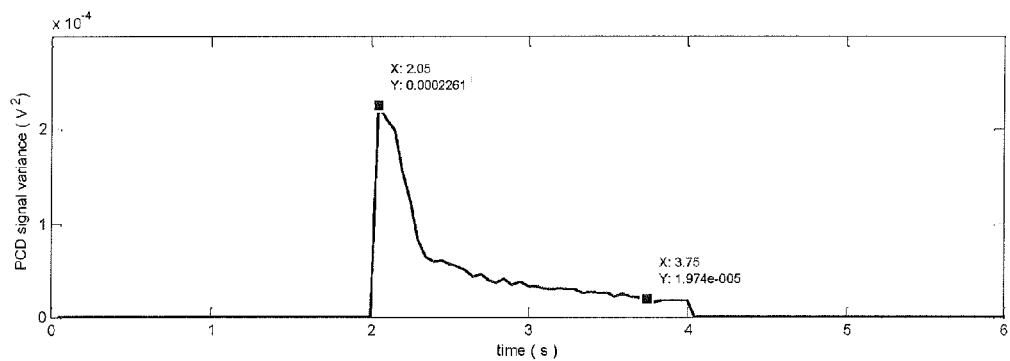
FIG. 2 is a graph showing the decay in cavitation detector signal variance during a pulsed ultrasound insonation in the system of FIG. 1.

Referring to FIG. 2, in the system such as that of FIG. 1, if a sample of tissue is targeted with a pulsed ultrasound signal, in this case with around 100 µs between pulses, the inertial cavitation starts quite abruptly, but then decays over time during the ultrasound exposure, in this case over about 2 s, in the absence of any kind of active cavitation control. FIG. 2 shows the variance of the detector signal $\sigma^2$ as a function of time. It can be seen from this that the signal variance gives a clear indication of the level of cavitation and how it changes over time.

Figure 3:
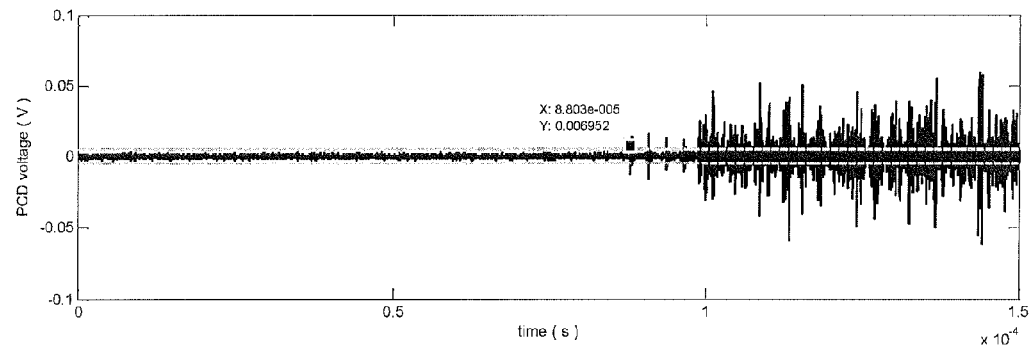
FIG. 3 is a graph showing detector signal as a function of time during a pulsed ultrasound insonation in the system of FIG. 1.

Referring to FIG. 3, at the start of an ultrasound pulse, the distance of the closest part of the cavitation cloud to the detector 12 can be determined by measuring the time between the start of transmission of the ultrasound pulse by the HIFU transducer 11 and the time at which the detector signal first increases above the background noise level. FIG. 3 shows an example of a raw output voltage trace from the PCD 12. The broken horizontal lines show the threshold voltage that is used to define the level of background noise, and the signal first exceeds this level at a time of about $0.9 \times 10^{-4}$ seconds. Thereafter the signal continues to vary significantly outside this threshold voltage. The time at which the signal first exceeds the threshold level can be used to determine the distance from the detector to the front of the cavitation bubble cloud, i.e. the closest part of the cavitation cloud to the HIFU transducer 11. This measurement can be repeated for each ultrasound pulse, so that the position of the cavitation cloud can be monitored over time.

Figure 4:
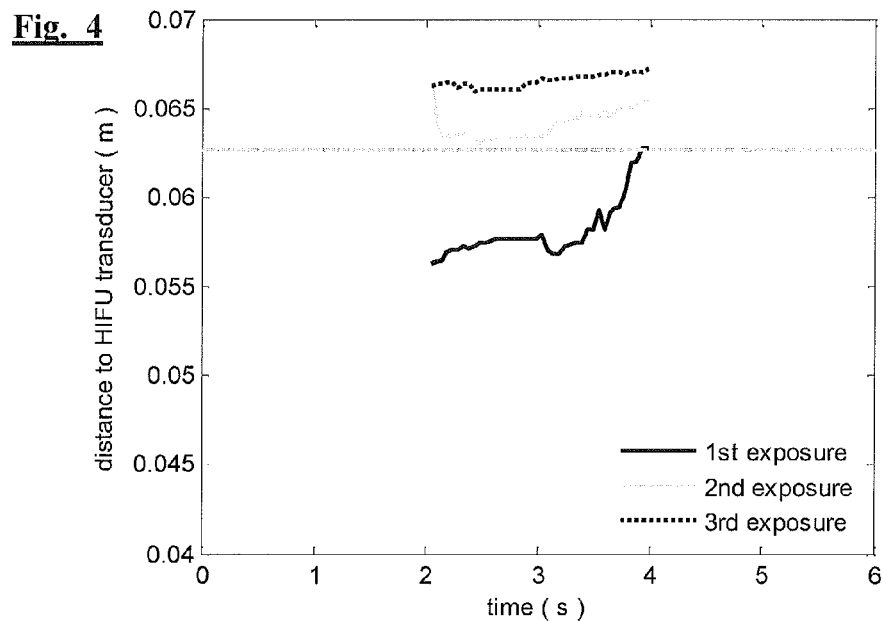
FIG. 4 is a plot showing position of cavitation relative the transducer in the system of FIG. 1 during each of three pulsed ultrasound insonation periods.

Referring to FIG. 4, the position of the front of the cavitation cloud varies over time during any exposure to ultrasound. In FIG. 4, the three traces show the distance between the ultrasound transducer 11 and the front of the cavitation cloud over the cavitation period of about 2 s in each of three separate exposures of pulsed ultrasound. As can be seen, the distance varies considerably between exposures, and also varies significantly over the course of each exposure.

Figure 5:
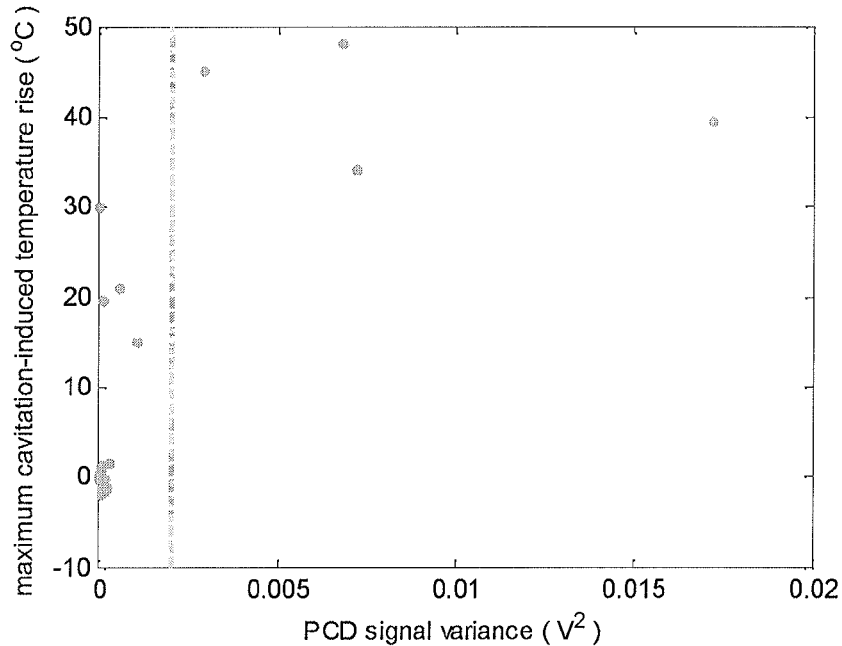
FIG. 5 is a graph showing variation of cavitation-induced temperature with cavitation detector signal variance in the system of FIG. 1.
Figure 6:
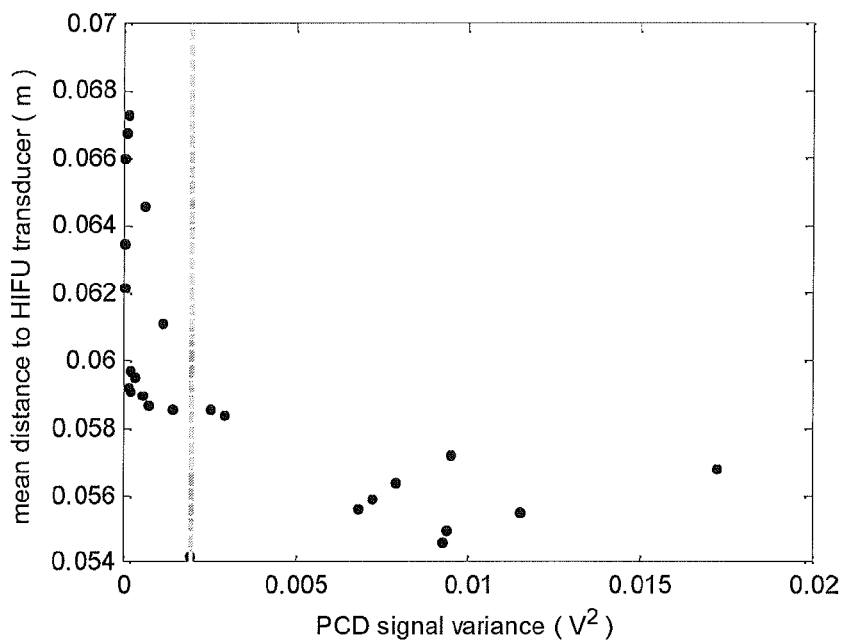
FIG. 6 is a graph showing variation of position of cavitation with cavitation detector signal variance in the system of FIG. 1.

In order to control treatment using the system of FIG. 1, it is necessary to know how the cavitation itself and its effects, which are the parameters to be controlled, vary with the parameters which can be directly measured. In this case, the variance of the detector signal is measured, and is generally indicative of the level of cavitation. Variations in the level of cavitation result in variation in the induced temperature rise and the position of the cavitation cloud. In order to measure the relationship between detector signal variance and temperature rise, a test sample (such as a phantom or excised tissue) is placed at the focal point 14, and pulsed ultrasound used to insonate the sample over a test period. During the insonation, the temperature of the sample is measured using a thermometer, while the detector signal variance $\sigma^2$ is also measured. The results of this process are shown in FIG. 5, which shows that the cavitation induced temperature rise increases significantly with signal variance for low levels of variance (and hence cavitation), but then reaches a plateau. During this test process, the distance of the cavitation cloud from the ultrasound transducer 11 can also be measured as a function of signal variance, and the results from several such exposures are shown in FIG. 6. It can be seen that the cavitation cloud tends to get closer to the transducer 11 as the variance increases, which is consistent with the cloud increasing in size as the level of cavitation increases. From these two graphs a target signal variance, shown by the vertical broken line, can be chosen, which provides sufficient temperature rise without the cavitation cloud getting too large, and therefore affecting too great a volume of tissue. This target signal variance can then be used to define a setpoint value, or range, of the variance for use in control of the system as will be described below.

Figure 7:
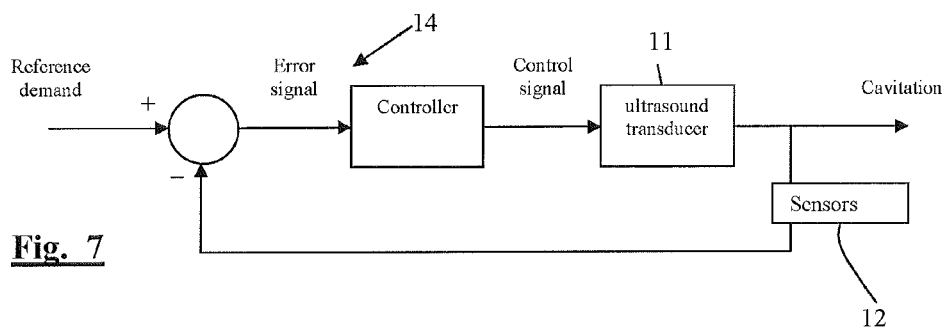
FIG. 7 is a high level system diagram showing operation of the system of FIG. 1.

Referring to FIG. 7, the controller 14 is arranged to operate on a closed loop control basis. The controller 14 is arranged to provide control signals to the ultrasound transducer 11, so as to control the amplitude and other parameters of the ultrasound generated. The detector 12 is arranged to sense any cavitation produced, and send sensor signals back to the controller 14. The controller is also arranged to receive a reference demand, which may correspond to a value or range of values of a parameter of the sensor signals, to compare the sensor signals, or the appropriate parameter of the sensor signals defined by the reference demand, with the reference demand and to calculate an error, and then to adjust the control signals if the error meets conditions stored in the controller. In other embodiments this basic feedback system can take many forms depending on the nature of the detector 12, which can be different from the PCD 12 as described above, on the parameter of the cavitation that is to be controlled, and on the relationship between that parameter and the parameter of the cavitation that can be directly measured, or the parameter of the sensor signals.

Figure 8:
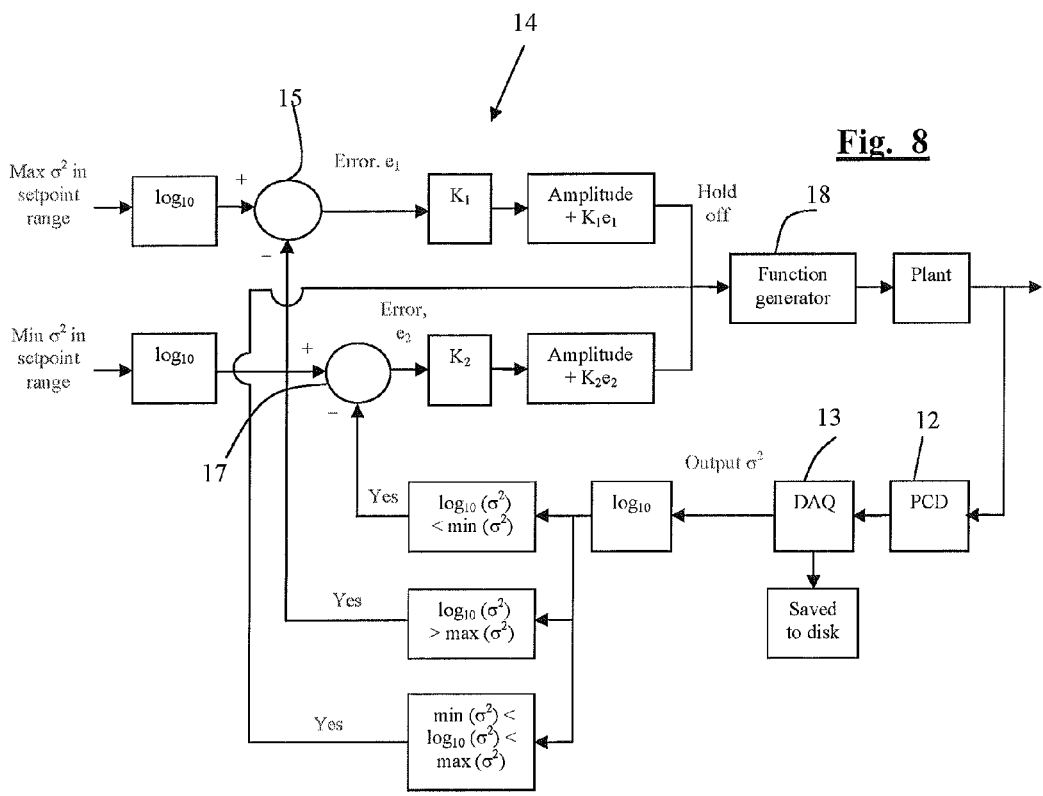
FIG. 8 is a functional flowchart showing operation of the system of FIG. 1.

Referring to FIG. 8, in this particular embodiment, the controller is arranged to receive the voltage signal V from the PCD 12, and includes a data acquisition card (DAQ) 13 which feeds digitized data to a software routine running on a computer, enabling calculation of the variance $\sigma^2$ of that voltage signal. The controller has stored in it a setpoint range of variance values, defined as maximum and minimum values of the variance $\sigma^2$. This setpoint range is based around the target variance value shown in FIGS. 5 and 6. This setpoint range forms a reference demand, and can be input and updated depending on the nature of the cavitation that is required. The controller is arranged to calculate the log of the measured detector signal variance and the log of the max and min setpoint variances, and to compare the log of the measured variance with the logs of the max and min values, and to control the amplitude of the drive signal to the transducer depending on the result. The part of the controller 14 that generates the drive signals for the HIFU transducer 11 is referred to as the function generator 18, and this controls the amplitude, as well as any other appropriate parameters, of the ultrasound generated by the HIFU transducer 11. If the measured variance $\sigma^2$ is within the desired range between the max and min values, then the function generator 18 that generates the control signal is arranged to keep the amplitude of the drive signal constant. If the measured variance is greater than the maximum variance, then a comparator 15 calculates an error $e_1$, which is the amount by which it is too high. The controller then calculates a reduced amplitude, reducing the current amplitude by a correction value, calculated as the product of the error $e_1$ and a first gain factor $k_1$, which is input to the function generator. If the measured variance is less than the minimum variance, then a separate comparator 17 calculates an error $e_2$, which is the amount by which it is too low. The controller then calculates an increased amplitude, increasing the current amplitude by a correction value, calculated as the product of the error $e_2$ and a second gain factor $k_2$, which is input to the function generator. The function generator 18 therefore alters the amplitude of the control signal to the transducer 11 so as to keep the PCD detector signal variance, and hence the level of cavitation, within the desired range of values.

Figure 9:
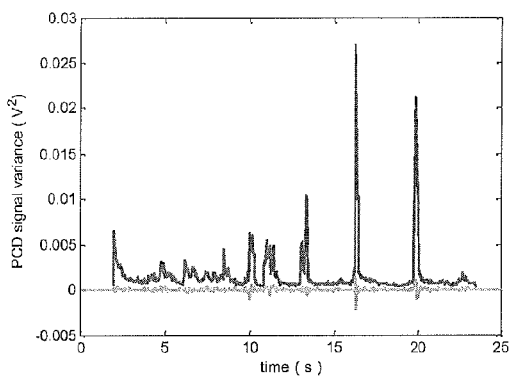
FIG. 9 is a graph of detector signal variance over time for different frequencies during operation of the system of FIG. 1 with cavitation control.
Figure 10:
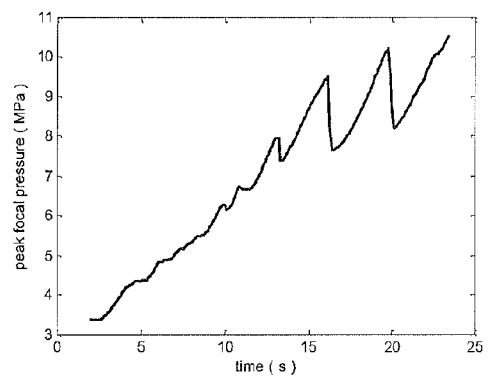
FIG. 10 is a graph of peak focal pressure over time during operation of the system of FIG. 1 with cavitation control.
Figure 11:
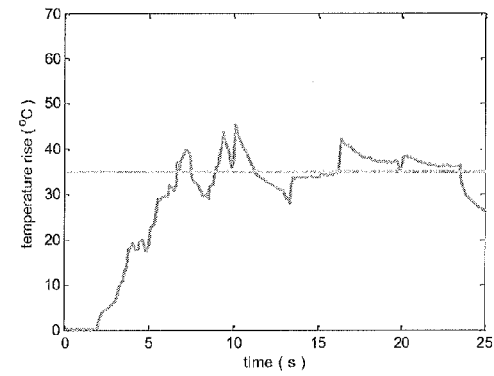
FIG. 11 is a graph of temperature over time during operation of the system of FIG. 1 with cavitation control.
Figure 12:
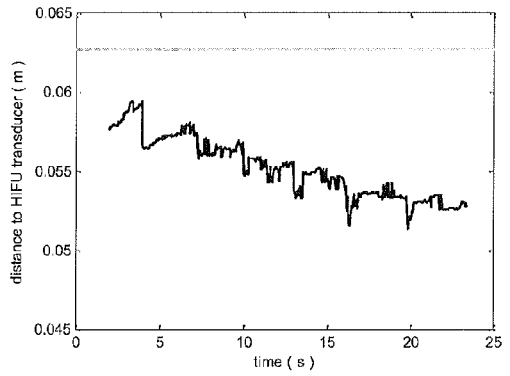
FIG. 12 is a graph of cavitation cloud position over time during operation of the system of FIG. 1 with cavitation control.

Referring to FIGS. 9 to 12 it can be seen that the control system described above can maintain cavitation for an extended test period of, in this case, over 20 s. In FIG. 9 the upper line is a plot of PCD signal variance over time for a broadband ultrasound frequency range indicative of inertial cavitation in the system of FIG. 8. The lower line is a plot of variance for frequencies corresponding to harmonic emissions indicative of stable cavitation. It can be seen that, while it varies significantly, some level of cavitation is maintained throughout the 20 s period. It can also be seen that the variances for the broadband and harmonic frequencies vary in different ways over time. Because they generate ultrasound of different frequency content, the different types of cavitation activity can be detected and controlled separately. FIG. 10 shows the peak focal pressure, i.e. the amplitude of the ultrasound output of the ultrasound transducer, as controlled by the controller 14. As can be seen, this pressure, and hence the output power of the transducer, increases steadily to maintain the cavitation. The peaks in the focal pressure are a result of the gain values used in the feedback control. FIG. 11 shows the resulting temperature of the sample through the 20 s period. As can be seen this rises up to a target temperature, shown by the broken line, and then fluctuates around that level throughout the 20 s period. This shows good control of the tissue temperature which can be used to provide controlled treatment. FIG. 12 shows how the distance between the front edge of the cavitation cloud and the transducer 11 varies during the test period. In this case the distance decreases steadily throughout the test period, but remains within acceptable limits.

For comparison, FIGS. 13 to 15 show the detector signal variances, the temperature increase, and the distance from cavitation cloud to ultrasound transducer for a pulsed ultrasound signal with a fixed peak focal pressure of 7.3 MPa, and FIGS. 16 to 18 are similar plots for a fixed 10.5 MPa peak focal pressure. As can be seen, in each case, the temperature rise starts significantly higher than desired, and is not maintained, falling below the desired level quite quickly.

The controller of FIG. 8 can be modified in various ways to provide further or alternative types of control. For example, the position of the cavitation cloud, as measured by its distance from the ultrasound transducer, can be used as a control input. The response of the controller to that data can be very simple. For example a threshold distance can be defined and, if the distance becomes less than that threshold, the transducer 11 can be switched off and the ultrasound transmission ended, on the assumption that heat is being applied to a region of tissue where it is not desirable. Alternatively a set point range of acceptable values for that distance can be defined, and the control signal amplitude varied so as to maintain the distance within the setpoint range. The system can be arranged to control just bubble cloud position, and not the degree of cavitation. Alternatively it can be arranged to control both cloud position and the degree of cavitation, in which case both of these can be measured, as described above, and the ultrasound amplitude controlled so as to obtain the best compromise, or combination, of cloud position and degree of cavitation. In some embodiments, or under some circumstances, it may be desirable to avoid cavitation altogether. In that case the target value of the PCD signal variance can be set to zero, or a target range of PCD signal variance set with a low upper limit. The system is then arranged to modify or stop the ultrasound transmission when cavitation is detected so as to bring the PCD signal variance back to the target value or range.

In a further modification the controller is arranged to measure the detector signal variance for both the broadband range and a range of harmonics of the transducer frequency. It can then monitor variations in the relative magnitudes of those variances which can be used as an indication of changes in the type of cavitation activity. The driving signal for the ultrasound transducer can be controlled in response to these changes to control the type of cavitation activity being produced.

While the examples described above rely on varying the amplitude of the driving signal to the ultrasound transducer, and hence the amplitude of the ultrasound waves generated in the subject, other parameters of the driving signal and hence of the ultrasound generated can also be varied by the feedback control. For example the frequency of the ultrasound can be varied, or where the ultrasound is pulsed, the pulse duration, duty cycle, or pulse repetition frequency can be varied. Rather than having a single ultrasound transducer, two or more transducers can be included in the system. This gives greater control over the position of the cavitation being produced, as the relative amplitudes of the transducers can be controlled to control the focus or centre of the cavitation.

Similarly other types of sensor can be used to measure, directly or indirectly, parameters of the cavitation produced, or the resultant heating generated, and these parameters can be used as at least a part of the feedback signals for the feedback control. For example, rather than a single detector, an array of ultrasound detectors, i.e. pressure sensors, can be used. The signals from these sensors, filtered so as to be sensitive to cavitation, can be used to locate the cavitation in two or three dimensions, rather than simply in one dimension as described above. Such a sensing system can be used together with multiple ultrasound transducers to provide control of cavitation position in two or three dimensions.

In each case where the control is based on feedback using an error between a measured parameter and a setpoint value or range for that parameter, the setpoint can be determined by varying the drive signals to the ultrasound transducer or transducers so as to produce a variation in the cavitation and hence a variation in the measured parameter, and also measuring a further parameter, such as tissue temperature or other therapeutically desirable bioeffect such as cell permeability, drug diffusion lengthscale, etc, and identifying the setpoint value or range of the measured parameter that corresponds to a desired value of the further parameter. This can be done in a similar way to that described above with reference to FIGS. 5 and 6. Once the setpoint range has been determined, suitable gain factors can be determined for the feedback control. The setpoint values and the gain factors are then stored in memory in the controller so that it can be used for cavitation control.

Embodiments of the invention provide both a procedure and the implementation of an adaptive feedback controller that utilizes the signal received from one or several passive cavitation detectors (PCD) to affect the input signal to the therapeutic ultrasound transducer(s) in order to both maintain and localize cavitation activity for prolonged periods of time. The controller has thus far been implemented in the context of maximizing cavitation-enhanced heating, but the procedures are directly extendable to optimizing other therapeutically desirable bioeffects and could also extend to applications outside the biomedical arena, for example in ultrasound cleaning baths, cavitation control in nuclear reactors, etc.

The invention claimed is:

1. An ultrasound system comprising a transducer, a controller arranged to generate control signals arranged to control the transducer to generate pressure waves directed at a target volume thereby to generate cavitation at a position in the target volume, and at least one sensor arranged to sense the cavitation and to output sensing signals, wherein the controller is arranged to: define a parameter of the sensing signals which is dependent on the position of the cavitation; define a target range of the parameter corresponding to a target range of the position; receive the sensing signals from the at least one sensor; measure a value of the parameter for the received sensing signals; determine whether the value is outside the target range and to change the control signals in response to the parameter being outside the target range thereby to maintain the position of the cavitation within the target range.

2. A system according to claim 1 wherein the pressure waves are arranged to produce the cavitation in an amount which varies, and the controller is further arranged to measure, from the sensing signals, variations in the amount of the cavitation, and to vary the control signals thereby to control the amount of the cavitation.

3. A system according to claim 2 wherein the cavitation is of a type which varies, and the controller is further arranged to measure, from the sensing signals, variations in the type of the cavitation, and to vary the control signals thereby to control the type of the cavitation.

4. A system according to claim 1 wherein the at least one sensor comprises at least one pressure wave detector arranged to detect pressure waves generated by the cavitation.

5. A system according to claim 4 wherein the controller is arranged to measure an arrival time of pressure waves at the at least one pressure wave detector, and to use the arrival time as the parameter.

6. A system according to claim 1 wherein the controller is arranged to measure the frequency content within one or more frequency bands of the pressure waves generated by cavitation and detected by the at least one pressure wave detector.

7. A system according to claim 1 wherein the controller is arranged to vary the control signals in real time in response to the sensing signals thereby to control the cavitation in real time.

8. A system according to claim 7 wherein the pressure waves are arranged to produce the cavitation in an amount which varies, and the controller is further arranged to measure, from the sensing signals, variations in the amount of the cavitation, and to vary the control signals thereby to control the amount of the cavitation.

9. A system according to claim 7 wherein the cavitation is of a type which varies, and the controller is further arranged to measure from the sensing signals variations in the type of the cavitation, and to vary the control signals thereby to control the type of the cavitation.

10. A method of controlling cavitation in a subject comprising: generating pressure waves directed at a target volume to cause cavitation in the target volume, sensing changes in the cavitation in the target volume using a sensor arranged to detect pressure waves generated by the cavitation and output sensor signals in response to detection of the pressure waves; defining a parameter of the sensor signals that is dependent on the position of the cavitation; defining a target range of the parameter corresponding to a target range of the position; receiving the sensor signals from the sensor; measuring a value of the parameter for the received signals, determining whether the measured value of the parameter is outside the target range of the parameter; and changing the generated pressure waves in response to the parameter being outside the target range thereby to maintain the position of the cavitation within the target range.

11. A method according to claim 10 wherein the sensor comprises a pressure wave detector, the method including measuring an arrival time of pressure wave at the pressure wave detector thereby to measure a position of the cavitation.

12. A method of setting up a pressure wave control system comprising producing a control signal to control a pressure wave transmitter so as to produce cavitation in a subject; sensing the cavitation using at least one sensor arranged to output a sensing signal indicative of a parameter of the cavitation; varying the control signal thereby to vary the cavitation; defining a sensing parameter of the sensing signal; measuring the values of a controlled parameter of the subject which is to be controlled by the pressure wave control system; measuring corresponding values of the sensing parameter; determining from the measured values how the sensing parameter varies with variations in the controlled parameter; and selecting a target range of the sensing parameter corresponding to a target value of the controlled parameter.

13. A method according to claim 12 wherein the at least one sensor comprises a pressure sensor arranged to detect pressure waves generated by the cavitation.

14. A method according to claim 13 wherein the controlled parameter comprises at least one of: a temperature, a position of the cavitation, an amount of mass transport, a measure of thermal damage, and a measure of mechanical damage due to cavitation.

15. An ultrasound system comprising a transducer, a controller arranged to generate control signals arranged to control the transducer to generate pressure waves directed at a target volume thereby to produce cavitation in the target volume, in an amount which is variable, and at least one sensor arranged to detect cavitation in the target volume and output sensing signals, wherein the controller is arranged to: receive the sensing signals from the at least one pressure wave detector; define a parameter of the signals which is dependent on the amount of the cavitation; define a target range of the parameter; determine from the sensing signals a measured value of the parameter; generate an error signal in response to the parameter being outside the target range; define a gain factor; and change the control signals by an amount dependent on the error signal and the gain factor, thereby to control the amount of the cavitation, wherein the gain factor is dependent on whether the measured value of the parameter is above or below the target range.

16. A system according to claim 15 wherein the sensing signals are arranged to have a variance, and the controller is arranged to calculate the variance of the sensing signals and to use the variance as the parameter.

17. An ultrasound system comprising: a transducer; a controller arranged to generate control signals arranged to control the transducer to generate pressure waves directed at a target volume thereby to generate cavitation at a position in the target volume; and at least one sensor arranged to sense the cavitation and to output sensing signals; wherein the controller is arranged to: define a parameter of the frequency content of the sensing signals which is dependent on the type of the cavitation; define a target range of the parameter corresponding to a target type of the cavitation; receive the sensing signals from the at least one sensor; measure a value of the parameter for the received sensing signals; determine whether the measured value of the parameter is outside the target range; and to change the control signals in response to the parameter being outside the target range thereby to control the type of the cavitation.

18. A system according to claim 17 wherein the at least one sensor comprises a pressure wave detector arranged to detect pressure waves generated by the cavitation, and the controller is arranged to define at least one frequency band of the pressure waves generated by the cavitation and to determine a frequency content of the detected pressure waves within the at least one frequency band, and wherein the parameter is the frequency content.

* * * * *